United States Patent
Baker et al.

(10) Patent No.: US 6,780,427 B2
(45) Date of Patent: *Aug. 24, 2004

(54) REDUCTION OF ADHESIONS USING CONTROLLED DELIVERY OF ACTIVE OXYGEN INHIBITORS

(75) Inventors: Keith Baker, Lynn, MA (US); Arthur J. Coury, Boston, MA (US)

(73) Assignee: Genzyme Corporation, Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 187 days.

(21) Appl. No.: 09/123,137

(22) Filed: Jul. 27, 1998

(65) Prior Publication Data

US 2001/0046503 A1 Nov. 29, 2001

Related U.S. Application Data

(63) Continuation of application No. 08/689,139, filed on Jul. 29, 1996, now Pat. No. 5,785,993, which is a continuation of application No. 08/410,219, filed on Mar. 24, 1995, now abandoned.

(51) Int. Cl.[7] ............................ A61K 9/127; A61K 9/16; A61K 9/52
(52) U.S. Cl. ..................... 424/450; 424/78.08; 424/400; 424/484; 424/459; 534/2; 534/261; 534/963; 534/944; 534/579
(58) Field of Search ................................ 424/400, 484, 424/489, 78.08; 514/2, 261, 944, 963, 579

(56) References Cited

U.S. PATENT DOCUMENTS

| | | |
|---|---|---|
| 4,371,519 A | 2/1983 | Hettinger |
| 4,511,478 A | 4/1985 | Nowinski et al. |
| 4,526,938 A | 7/1985 | Churchill et al. |

(List continued on next page.)

FOREIGN PATENT DOCUMENTS

| | | | |
|---|---|---|---|
| EP | 0 138 111 A1 | | 4/1985 |
| EP | 0 138 111 B1 | | 4/1985 |
| EP | 0 357 240 | | 3/1990 |
| EP | 0 372 969 | | 6/1990 |
| WO | WO 91/11992 | | 8/1991 |
| WO | WO 9316687 | | 9/1993 |
| WO | 9317669 | * | 9/1993 |
| WO | WO 93/19660 | | 10/1993 |
| WO | WO 94/24962 | | 1/1994 |
| WO | WO 94/21324 | | 9/1994 |
| WO | WO 95/29666 | | 3/1995 |

OTHER PUBLICATIONS

Sawney et al. in Biomaterials 14, p 1008–1016, 1993.*
Technical Bulletin UNIMED, 1992.*
Sawney et al. J. Biomed. Mels. Res. 28 p 831–838 (1994).*
Arras, et al. "The delivery of angiogenic factors to heart by microsphere therapy," *Nature Biotechnology* 16:159–162 (1998).

(List continued on next page.)

*Primary Examiner*—Thurman K. Page
(74) *Attorney, Agent, or Firm*—Pabst Patent Group LLP

(57) ABSTRACT

SOD and other active oxygen inhibitors are directly applied in combination with a barrier material at local sites of tissue injury to prevent or decrease formation of adhesions and undesirable proliferation of cells. Preferred barrier materials are polymeric hydrogels providing controlled release of AOI which are directly applied to the afflicted tissue. Examples demonstrate the effects of SOD on pelvic adhesions in the rat when administered by intraperitoneal (I.P.) bolus and by localized sustained release from a topically applied hydrogel system.

22 Claims, 2 Drawing Sheets

U.S. PATENT DOCUMENTS

| | | | |
|---|---|---|---|
| 4,563,349 A | 1/1986 | Miyata et al. | |
| 4,603,695 A | 8/1986 | Ikada et al. | |
| 4,741,872 A | 5/1988 | De Luca et al. | |
| 4,745,161 A | 5/1988 | Saudek et al. | |
| 4,760,051 A | 7/1988 | Pickart | |
| 4,804,691 A | 2/1989 | English et al. | |
| 4,806,621 A | 2/1989 | Kohn et al. | |
| 4,826,945 A | 5/1989 | Cohn et al. | |
| 4,873,292 A | 10/1989 | Ogata et al. | |
| 4,888,413 A | 12/1989 | Domb | |
| 4,889,722 A | 12/1989 | Sheffield et al. | |
| 4,897,308 A * | 1/1990 | Vanlerberghe | 428/402.2 |
| 4,898,734 A | 2/1990 | Mathiowitz et al. | |
| 4,911,926 A | 3/1990 | Henry et al. | |
| 4,925,677 A | 5/1990 | Feijen | |
| 4,937,254 A | 6/1990 | Sheffield et al. | |
| 4,938,763 A | 7/1990 | Dunn et al. | |
| 4,942,035 A | 7/1990 | Churchill et al. | |
| 4,957,744 A | 9/1990 | della Valle et al. | |
| 4,976,959 A | 12/1990 | Berger, Jr. et al. | |
| 4,994,277 A | 2/1991 | Higham et al. | |
| 5,066,590 A | 11/1991 | Yabuki et al. | |
| 5,100,992 A | 3/1992 | Cohn et al. | |
| 5,108,755 A | 4/1992 | Daniels et al. | |
| 5,126,141 A | 6/1992 | Henry | |
| 5,135,751 A | 8/1992 | Henry et al. | |
| 5,137,820 A | 8/1992 | Maeda et al. | |
| 5,143,731 A | 9/1992 | Viegas et al. | |
| 5,160,745 A | 11/1992 | De Luca et al. | |
| 5,175,235 A | 12/1992 | Domb et al. | |
| 5,213,580 A | 5/1993 | Slepian et al. | |
| 5,217,966 A | 6/1993 | Bruice | |
| 5,219,564 A | 6/1993 | Zalipsky et al. | |
| 5,223,538 A | 6/1993 | Fridovich et al. | |
| 5,227,405 A | 7/1993 | Fridovich et al. | |
| 5,260,204 A | 11/1993 | Heckl et al. | |
| 5,283,317 A | 2/1994 | Saifer et al. | |
| 5,286,763 A | 2/1994 | Gerhart et al. | |
| 5,288,502 A * | 2/1994 | McGinity | 424/484 |
| 5,292,516 A | 3/1994 | Viegas et al. | |
| 5,328,471 A | 7/1994 | Slepian | |
| 5,364,622 A | 11/1994 | Franz et al. | |
| 5,366,735 A | 11/1994 | Henry | |
| 5,384,333 A | 1/1995 | Davis et al. | |
| 5,419,917 A * | 5/1995 | Chen | 424/469 |
| 5,478,837 A | 12/1995 | Rodgers et al. | |
| 5,527,864 A | 6/1996 | Suggs et al. | |
| 5,561,158 A | 10/1996 | Yu et al. | |
| 5,562,594 A | 10/1996 | Weeks | |
| 5,589,169 A | 12/1996 | Mohler et al. | |
| 5,733,563 A * | 3/1998 | Fortier | 426/422 |
| 5,785,993 A * | 7/1998 | Baker | 424/450 |

OTHER PUBLICATIONS

Diamond, et al., "Adhesion reformation and de novo adhesion formation after reproductive pelvic surgery," *Fert. and Ster.* 47:864 (1987).

Dumanian, et al., "A New Photopolymerizable Blood Vessel Glue That Seals Human Vessel Anastomoses Without Augmenting Thrombogenicity," *Plastic and Reconstructive Surgery* 95(5):901–907 (1995).

Dunn, et al., "Synergistic effect of intraperitoneally administered calcium channel blockade and recombinant tissue," *Am. J. Obstet. Gynecol*, 164:1327–1330 (1991).

Fridovich, "Biological Effects of the Superoxide Radical," *Arch. Bioch. & Biophys.* 247:1–11 (1986).

Haney, A.F., "Murine peritoneal injury and de novo adhesion formation caused by oxidized–regenerated cellulose (Interceed*[TC7]) but not expanded polytetrafluoroethylene (Gore–Tex* Surgical Membrane)," *Fertiltiy and Sterility* 57:202–208 (1992).

Hill–West, et al., "Prevention of Postoperative Adhesions in the Rat by In Situ Photopolymerization of Bioresorbable Hydrogel Barriers," *Obstet. Gynecol.* 83:59–64 (1994).

Hom et al., "Vascular effects of sustained–release fibroblast growth factors," *Ann. Otol. Rhinol. Laryngol.*, 105:109–116 (1996).

Kontos, et al., "Oxygen Radicals in Brain Injury," *CNS Trauma* 3:257–263 (1986).

Luciano, et al., "A Comparative Study of Postoperative Adhesions Following Laser Surgery by Laparoscopy Versus Laparotomy in the Rabbit Model," *Obstet. & Gyn.* 74:220 (1989).

Luciano, et al., "A comparison of thermal injury, healing patters, and postoperative adhesion formation following $CO_2$ laser and electromicrosurgery," *Fert. and Ster*, 48:1025 (1987).

Monk, et al., "Adhesions after extensive gynecologic surgery: Clinical significance, etiology, and prevention," *Am. J. Obstet. Gynecol*, 170:1396–1403 (1994).

Odlind, et al., "Tissue Distribution of $^{125}$I–Labelled Bovine Superoxide Dismustase (SOD) in the Rat," *Pharmacol. Toxic* 62:95–100 (1988).

Peters, et al., "A randomized clinical trial on the benefit of adhesiolysis in patients with intraperitoneal adhesions and chronic pelvic pain," *Br. J. Obstet. Gyn.* 99:59 (1992).

Petkau, et al., "Tissue Distribution of Bovine $^{125}$I–Superoxide Dismutase in Mice," *Res. Commun. Chem. Pathol. Pharmacol*, 15:641–654 (1976).

Pijlman, et al., "Prevention of adhesions," *Eur. J. Obst. & Gyn. Repro. Biol.* 53:155–163 (1994).

Portz et al, "Oxygen Free Radicals and Pelvic Adhesion Formation: I. Blocking Oxygen Free Radical Toxicity to Prevent Adhesion Formation in an Endometriosis Model," *Int. J. Fertil.* 36:39–42 (1991).

Pyatak, et al., "Preparation of a Polyethylene Glycol: Superoxide Dismutase Adduct, and as Examination of its Blood Circulating Life and Anti–Inflammatory Activity," *Res. Comm. Chem. Path. Pharm.* 29:113–127 (1980).

Rodgers, et al., "Partial Splenectomy for Gaucher's Disease," *Ann. Surg.* 205:693–698 (1987).

Schneider, et al., "Comparison of the Protective Effects by Human and Bovine Superoxide Dismutase Against Ischemia–and Reperfusion–Induced Impairment of Kidney Function in Anesthetized Rats," *Fr. Rad. Biol. & Med.* 3:21–26 (187).

Schwartz, et al., "Formation, Reduction, and Treatment of Adhesive Disease," *Sem. in Repro. Endocrin.* 9:89–99 (1991).

Steinleitner, Alex, et al., "An evaluation of Flowgel* as an intraperitonael barrier for prevention of postsurgical adhesion reformation," *Fertility and Sterility* 57:305–308 (1992).

Surrey, et al., "Second–Look Laparoscopy after Reconstructive Pelvic Surgery for Infertility," *J. Repro. Med.* 27:658 (1982).

Tsimoyiannis, et al., "The Role of Oxygen–Derived Free Radicals In Peritoneal Adhesion Formation Induced by Ileal Ischaemia/Reperfusion," *Acta Chir. Scand.* 155:171–174 (1989).

Tulandi, Effect of Ringer's Lactate on Postsurgical Adhesion. In: Diamond, et al., eds, vol. 381, *Progress in Clinical and Biological Research* (NY, Wiley–Liss 1993) 149–153.

Voogd, et al., "Contradictory Effects of Superoxide Dismutase After Global or Regional Ischemia in the Isolated Rat Heart," *Fr. Rad. Biol. & Med.* 11:71–75 (1991).

Zimmerman, et al., "Mechanisms of Reperfusion Injury," *Am. J. Med. Sci.* 307:284–292 (1994).

"Arthritis Drug in UK Trials," *Chemical Marketing Reporter* p. 19 (Mar. 19, 1990).

"PEG–superoxide dismutase reported to be of benefit in head injury," *The Pharmaceutical Journal* (Jul. 31, 1993).

* cited by examiner

REDUCTION OF ADHESIONS USING CONTROLLED DELIVERY OF ACTIVE OXYGEN INHIBITORS

This application is a continuation of Ser. No. 08/689,139, filed Jul. 29, 1996, now U.S. Pat. No. 5,785,993, which is a continuation of Ser. No. 08/410,219, filed Mar. 24, 1995, now abandoned.

BACKGROUND OF THE INVENTION

The present invention is generally in the area of prevention of surgical adhesion.

Adhesions are a common complication of surgery. They may develop in a variety of areas in the body, and are characterized in that tissues which were separate before surgery become bonded together in the process of healing. The type and degree of damage caused by adhesions is variable, ranging from life-threatening, as in the intestines due to blockage, to extremely disabling, as in tendons or spinal cord, to chronic pain and infertility in the pelvic cavity, to being obstructive of further surgery in the pericardium. Postoperative formation of pelvic adhesions remains a serious problem in patients undergoing gynecological surgery and is a principal cause of infertility. In general, the most common causes of pelvic adhesions in women are prior surgery, endometriosis and pelvic inflammatory disease.

Injury to intact peritoneum as a result of surgical insult or infection begins a cascade of pathophysiological events. Within three hours of surgical insult or infection, there is damage to vasculature, resulting in increased vessel permeability, and an inflammatory response, resulting in further vascular damage due to ischemia and reperfusion injury. The exudate of serosanguionous fluid and fibrin matrix leads to further ischemia, resulting in persistence of fibrin matrix and collagenous adhesions, as well as fibrinolysis to yield fibrin split products, absorption of fibrin matrix, and normal repairs. This cascade includes the expected events associated with inflammation including both neutrophil and macrophage migration to the site of inflammation. Associated with this cell migration is a rapid respiratory burst leading to the generation of oxygen radicals at the site of inflammation. In the absence of sufficient free radical scavengers, high concentrations of oxygen radicals are capable of damaging the surrounding intact cells, including those responsible for vascular integrity. This increased permeability of blood vessels can lead to exudation of proteinaceous serosanguinous fluid which serves as a matrix for fibrinous adhesions. In addition, increased vascular permeability leads to local interruption of blood flow and eventual cell death in the vessels comprising the vascular supply. Reperfusion of tissues, following this ischemic event, leads to further generation of oxygen radicals and, ultimately, further exacerbates the degree of fibrinous adhesion formation.

Under normal circumstances, the fibrinolytic capacity of plasminogen activator activity (PAA) leads to the absorption of such fibrinous deposits and to conventional peritoneal healing. However, in the presence of severe tissue injury (e.g. following surgical trauma), a decrease in PAA leads to abnormally persistent fibrin deposits and, ultimately, mature collagenous adhesions. Meticulous dissection (i.e. adhesiolysis) continues to be the most widely accepted treatment for existing adhesions. A substantial fraction of surgery therefore requires follow-up surgery to repair the effects of the adhesions. This procedure is generally called "adhesiolysis"; in some organ systems, the procedure has specific names, such as "tenolysis" in the freeing of tendons.

The list of potential therapeutic modalities used in prevention of formation and reformation of adhesions is extensive and includes infusion of liquids into the pelvic cavity at the time of surgery, mechanical barriers between two opposing surfaces, and intravenously injected or topically applied pharmacologic agents (Tulandi, "Effects of Ringer's Lactate on Postsurgical Adhesion. In: Diamon, et al., eds, vol. 381, Progress in Clinical and Biological Research (NY, Wiley-Liss 1993) 59–63; Schwartz, et al., *Sem. in Repro. Endocrin.* 9:89–99 (1991); Pjilman, et al., *Eur. J. Ost & Gyn. Repro. Biol.* 53:155–163 (1994); and Monk, et al., *Am. J. Obstet. Gynecol.* 170:1396–1403 (1994). However, the incidence of symptomatic adhesion formation remains high, and the clinical need for adhesion prevention still exists.

Therapies of various sorts have been used to prevent the initial formation of adhesions ("primary" adhesions). These include lavage with water-soluble polymers and/or biologically active molecules ("drugs"), which are usually not very effective. However, the use of superoxide dismutate (SOD) combined with catalase prevented or diminished endometriosis-induced adhesions in rabbits in a study by Poretz et al, (*Int. J. Fertil.* 36:39–42, 1991). Permanent mechanical barriers, such as Teflon™ sheets, can be effective but are difficult to remove; and degradable barriers such as oxidized cellulose (InterCeed™, Johnson & Johnson) and degradable polymeric gels (Sawhney et al, 1993; Hill-West et al 1994) can have significant utility in the prevention of primary adhesions. Tsimoyiannis et al (*Acta Chir. Scand.* 155: 171–174, 1989) reported reductions of about 50% in the incidence and 50–70% in the severity of ischemia-related induction of primary adhesions in rats, after administration of SOD, catalase, DMSO (dimethylsulfoxide) or allopurinol as an intravenous bolus before surgery.

It has been hypothesized that the commonality of these drugs is in their inhibition of the pathway leading to oxidative damage to tissue. SOD, catalase and DMSO each directly destroy active oxygen species, such as superoxide, peroxide, or hydroxyl radical; allopurinol is known to inhibit the enzyme xanthine oxidase, which produces hydrogen peroxide. These compounds which directly or indirectly inhibit the effect of active oxygen species on tissue are referred to herein as "active oxygen inhibitors", or AOIs. Superoxide dismutase (SOD, dimer MW=31.5 kDa, tetramer=67 kDa) has been efficacious in the treatment of ischemic/reperfusion events in a wide variety of tissues including brain, kidney, and heart (Schneider, et al., *Fr. Rad. Biol. & Med.* 3:21–26 (1987); Zimmerman, et al., *Am. J. Med. Sci.* 307:284–292 (1994); Voogd, et al., *Fr. Rad. Biol. & Med.* 11:71–75 (1991); Fridovich, *Arch. Bioch. & Biophys.* 247:1–11 (1986); Kontos, et al. *CNS Trauma* 3:257–263 (1986)). There is also evidence that SOD can be effective in the prevention of pelvic adhesions (Tsimoyiannis, et al., *Acta Chir. Scand.* 155:171–174 (1989); Portz, et al., *Int. J. Fert.* 36:39–42 (1991); O'Leary, et al., *Ann. Surg. June:*693–698 (1987)). However, efficacy using SOD has been limited, due to its rapid elimination from the bloodstream (Petkau, et al., *Res. Commun. Chem. Pathol. Pharmacol.* 15:641–654 (1976); Odlund, et al., *Pharmacol. Toxic* 62:95–100 (1988)). Improved efficacy has resulted from strategies for increasing SOD content in the bloodstream including chemical modification to reduce the rate of elimination (Pyatak, eta l., *Res. Comm. Chem. Path. Pharm.* 29:113–127 (1980); Hill-West, et al. *Obstet. Gynecol.* 83:59–64 (1994)) and frequently repeated injections (O'Leary, et al., 1987).

Removal of adhesions once formed is substantially more difficult than prevention of adhesion formation. Unfortunately, formulations which effectively prevent primary adhesions (e.g., Hill-West et al, 1994) can be substantially less effective in preventing re-adhesion after adhesiolysis ("secondary" adhesions). While the exact biological differences between primary and secondary adhesions are not known, it is possible that the formation of primary adhesions depends on the persistence of fibrin bridges between the disjoint parts, which are subsequently colonized by other cells and develop into permanent vascularized tissue. Anything disrupting formation or stabilization of the initial fibrin bridge would tend to prevent primary adhesion formation. Secondary ahesions, however, maybe the result of the normal healing process applied to injured pre-existing tissue, i.e. the lysed primary adhesion. The healing process, while not yet understood in detail, involves the mobilization of several cell types and the formation of new collagen, and typically has initial stages lasting for up to two weeks followed by several months of maturation to obtain full repair. Because of these differences, it is possible that treatments effective in primary adhesion prevention will require enhancement to prevent reformation of adhesions after adhesiolysis.

In summary, there have been no reports of compositions totally effective in eliminating adhesions, especially in patients in which the injury is repeated, as in the case of patients having had multiple surgeries.

It is therefore an object of the present invention to provide a method and compositions for preventing adhesions following surgery or infection.

SUMMARY OF THE INVENTION

SOD and other active oxygen inhibitors are directly applied in combination with a barrier material at local sites of tissue injury to prevent or decrease formation of adhesions and undesirable proliferation of cells. Preferred barrier materials are polymeric hydrogels providing controlled release of AOI which are directly applied to the afflicted tissue.

Examples demonstrate the effects of SOD on pelvic adhesions in the rat when administered by intraperitoneal (I.P.) bolus and by localized sustained release from a topically applied hydrogel system.

DETAILED DESCRIPTION OF THE INVENTION

Figure 1:
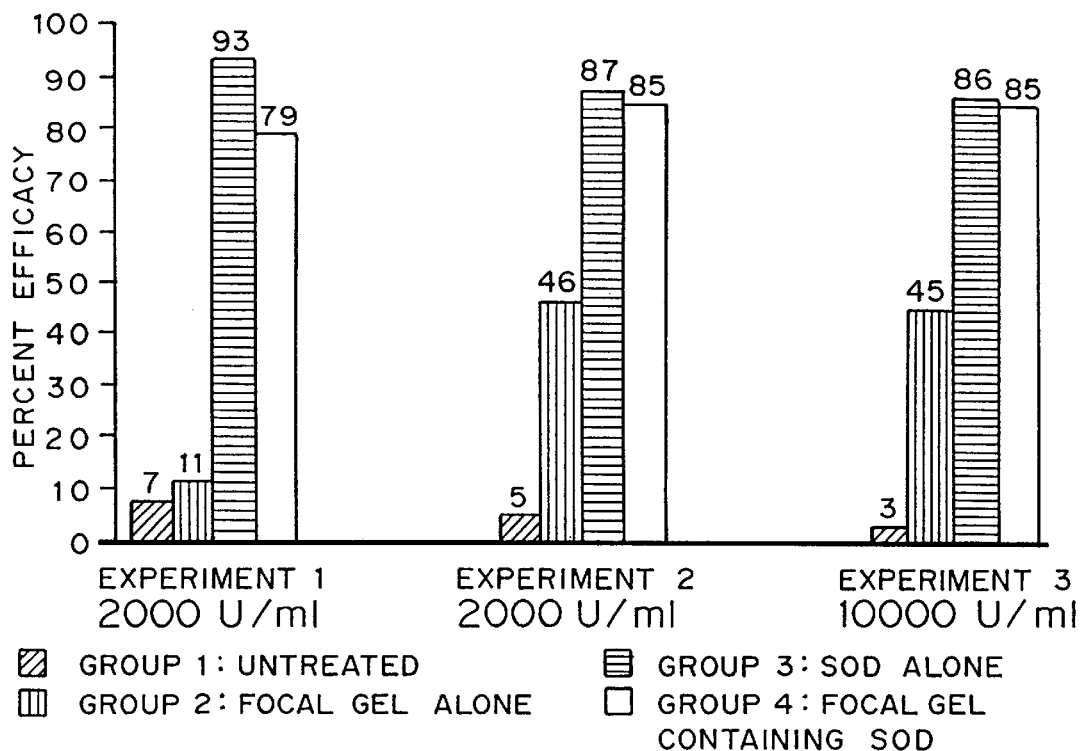
FIG. 1 is a bar graph of the percent efficacy in primary adhesions rat uterine horn model of treatment with hydrogel (|| || ||), SOD alone (≡), and SOD locally delivered via the hydrogel (open bar), as compared with untreated animals (/ / /) at dosages of 2000 U SOD/ml versus 10,000 U SOD/ml.

As described herein, a method and compositions providing for prevention or minimization of tissue adhesions, especially secondary tissue adhesions, is described where active oxygen inhibitors such as SOD are locally applied to the injured area in a hydrogel formulation. In the preferred embodiment, the hydrogel is polymerized in situ by photopolymerization of a biocompatible, biodegradable macromer solution such as a polyethylene glycol dilactide diacrylate. Alternatively, or in addition, a barrier material can be used in combination with the active oxygen inhibitor, as well as controlled release means for the active oxygen inhibitor ("AOI"). These materials, including the hydrogels, are generally referred to as "barrier materials" unless otherwise specified.

Barrier Materials:

Primary Barrier Materials:

Barrier materials can be administered as fluids, pastes, or other fluent forms, and locally altered in the body to form conforming barriers at or near the site of application, or as solid barriers. The barrier materials should be-biologically benign, and in particular, should not induce a severe local inflammatory response. Essentially all implants cause a transient local reaction after implantation. A benign, or biocompatible, material does not provoke a prolonged or escalating inflammatory response. Preferred barrier materials should be degradable or should dissipate within a reasonable time by exposure to natural body fluids. Preferred barrier materials should also serve as a depot for controlled release of AOIs over a period of hours to weeks, to allow local delivery directly to injured tissues.

A preferred barrier material is a gel, most preferably a gel material which is absorbed in vivo, whether by gradual dissipation into solution, spontaneous hydrolysis, enzymatic degradation, or a combination of these. Examples of suitable gels are the Pluronic® poloxamer gel systems are polyalkylene oxides, some members of which form gels at body temperature but are liquid at room temperature; and the photopolymerizable gels described by Hubbell et al (WO 93/17669) and Sawhney et al, *J. Biomed. Mats. Res.* 28, 831–838 (1994). Pluronic gel systems are known as anti-adhesion barriers (U.S. Pat. Nos. 4,911,926 and 5,135,751 to Henry et al; U.S. Pat. No. 5,366,735 to Henry) and as drug delivery vehicles (U.S. Pat. No. 5,292,516 to Viegas et al), as are the cited Hubbell materials.

Numerous other formulations are potentially capable of serving as barriers with drug delivery capability. These include the polymers of U.S. Pat. No. 4,938,763 to Dunn et al, U.S. Pat. No. 5,108,755 to Daniels et al, U.S. Pat. No. 4,913,903 to Sudmann et al, U.S. Pat. Nos. 5,100,992 and 4,826,945 to Cohn et al, U.S. Pat. No. 5,219,564 to Zalipsky et al, U.S. Pat. Nos. 4,741,872 and 5,160,745 to De Luca et al, U.S. Pat. Nos. 4,526,938 and 4,942,035 to Churchill et al, U.S. Pat. No. 4,888,413 to Domb, U.S. Pat. No. 4,511,478 to Nowinski et al, U.S. Pat. No. 4,957,744 to della Vallee et al, U.S. Pat. No. 4,925,677 to Feigen, U.S. Pat. No. 4,994,277 to Hingham et al, U.S. Pat. No. 5,364,622 to Franz et al and U.S. Pat. No. 4,804,691 to English et al. Hyaluronic acid materials, including hyaluronic acid gels and membranes, are also suitable for local delivery of AOIs to injured tissue.

Oxidized cellulose, administered as a fabric, forms a gel in bodily fluids and can deliver drugs (U.S. Pat. No. 4,889,722 to Sheffield et al). However, it is believed to be somewhat inflammatory and is therefore not preferred. Purely mechanical barriers, such as "Teflon®", fluoropolymer sheets and other non-degradable materials, are less desirable, but may be suitable if combined with other means for controlled local release of the drug directly to the injured tissue.

Although less preferred, gel barriers which are not readily degradable can be used. These include materials such as agarose, crosslinked polyacrylamide, gelled polyvinyl alcohol, gelled or crosslinked HEMA (poly hydroxymethyl acrylate), crosslinked dextran, and other known gelling materials. These can be very biocompatible, and are suitable for drug delivery.

The concentration of the gel-forming polymer in a hydrogel is variable, as is well-known. Suitable concentrations of polymer are those which give a gel which has adequate mechanical properties to persist at the site of application for at least the desired period of treatment, which will typically be days to weeks. Minimum effective gelling concentrations of various polymers range from as low as 0.1% (w/w) for ultrapure agarose, to between 3 and 5% for the polymers of Hubbell et al, to over 10% for some poloxamers such as Pluronics®-. Upper limits are imposed by solubility, by viscosity, by the onset of brittleness of the gel, by excessive swelling after formation, by osmotic effects of the applied monomers on tissue, and by a desire to minimize the amount of polymer applied in a treatment. These factors and their manipulation are known in the art, and vary with the polymer. Upper concentration limits may vary from as low as 2% for agarose, to between 25 and 30% for the polymers of Hubbell, to 50% or more for poloxamers.

Preferred materials for barriers and delivery means are characterized by certain critical characteristics, including: biocompatibility; delivery times extending from a day up to weeks; compatibility with the AOI to be delivered; and, in more preferred embodiments, biodegradability. Preferred materials contain at least some water, further containing physiologically-acceptable salts and buffers; higher levels of water are preferred, where otherwise compatible with mechanical and diffusional properties of the materials. It is preferred to combine the barrier function with the controlled-release function in a single material; of such materials, hydrogels are preferred.

As shown in the Examples below, a preferred mode is the incorporation of an AOI, preferably SOD, in a solution also containing a biocompatible, biodegradable, gel-forming photopolymerizable monomer, and suitable photoinitiators, buffers and stabilizers; delivery of the combined solution to a site where adhesiolysis has been performed, and covering the affected areas; and photopolymerizing the composition to create a barrier gel which slowly releases the AOI during a period of days to over a week.

As noted above, the concentration of the polymerizable material is variable. For the particular material used in the examples, the preferred concentration of the monomer is in the range of 10% to about 25% w/w in buffered isotonic saline solution. Higher concentrations tend to give slower and more prolonged release of the AOI, and to last longer as barriers, but are correspondingly more viscous, which can make application more difficult if done through a laparoscope or catheter. Other materials will have different preferred concentrations, as previously noted.

Drug Delivery Means.

Controlled delivery means can be employed in addition to a gel, or in place of a gel. There are a large number of physiologically-acceptable drug delivery materials known in the art which have the following properties:

1. The delivery means must be localizable, or at least potentially localizable, to allow the delivery of the contents primarily to a particular target organ or region. A suitable means, although not preferable for human use, is an osmotic pump, such as an Alzet® pump (Alza Co.)

2. The delivery means must be biocompatible, and in particular should not be substantially inflammatory in the body. Illustrative controlled delivery means include small particles of drug entrapped in a bioerodible polymer such as polyglycolide, polylactide or polyanhydride, for example, U.S. Pat. No. 4,898,734 to Mathiowitz et al; U.S. Pat. No. 5,175,235 to Domb; U.S. Pat. No. 5,286,763 to Gerhart et al; and U.S. Pat. No. 4,745,161 to Saudek et al, optionally coated with a release-retarding shell, which are in turn delivered to the site at which adhesions are to be prevented, preferably with additional means to retain them near the site, such as a barrier membrane or a gel. Controlled delivery means are especially important when the drug to be delivered has a high aqueous solubility and a low molecular weight.

3. Preferably, the delivery means will degrade in the body, concurrently with delivery of drugs or subsequently. Most of the polymers noted as potential hydrogel materials above are biodegradable, as are the polymers listed in the previous paragraph. Classical erodible polymers, such as poly(hydroxyacids) (e.g., polyglycolide, polylactide, and polycaprolactone) are suitable in many situations, although they are somewhat more inflammatory than some newer polymers.

Pharmaceutically Active Compounds

Active Oxygen Inhibitors.

As used herein, AOIs are defined as compounds which destroy, or prevent the formation of, active oxygen species. Active oxygen species include superoxides, peroxides in general, hydrogen peroxide, and hydroxyl radical (OH). Other active species derived from active oxygens, such as hypochlorite ion (OCl—), hydroxyl free radicals on carbohydrates, "singlet oxygen", or ozone, are also included. The active oxygen species damage tissue directly. Moreover, they may cause indirect damage by attracting cells to the site of injury, or otherwise stimulating an inflammatory response.

A preferred antioxidant drug is superoxide dismutase (SOD). It is thought that SOD prevents tissue damage and inflammation by destroying the superoxide radical. Any of the forms of SOD are suitable. Sources include human, which is preferred for minimization of immunogenicity, and also other known sources including bovine and bacterial; SOD from various tissues, such as liver, red cells, and others; SOD having any functional metal ion, such as manganese, iron, copper, and zinc. One form (manganese) of recombinant human SOD is described in U.S. Pat. No. 5,260,204 to Heckl et al, referencing EP-A 138111 to Chiron as a source of recombinant human copper/zinc SOD. Also included are SOD modified with pendant polymers, such as polyethylene glycol or polyvinyl alcohol; natural SOD produced by recombinant or transgenic processes; and variant forms of SOD produced by mutation or protein engineering. All of these processes are known in the art.

Alternative methods of delivery of SOD, or of other protein-based drugs of the antioxidant class, to the site include expression by transformed cells instilled at the site, and transient transformation of cells at the site by recombinant DNA including a mammalian promoter, such as a plasmid, an expression cassette, or a viral vector. These may be delivered locally by any suitable means, including liposomes, polymeric composites, in solution via catheters and other similar devices, via electroporation or iontophoresis, and by other methods known in the art.

Other drugs having antioxidant activity (i.e., destroying or preventing formation of active oxygen) may be used in the prevention of adhesions, either in combination with SOD, in combination with each other, or alone. Protein drugs include catalases, peroxidases and general oxidases or oxididative enzymes such as cytochrome P450, glutathione peroxidase, and other native or denatured hemoproteins. Most such molecules have detectable peroxidase activity. Small-molecule drugs may act by directly absorbing or inactivating active oxygen species. These include vitamin C (ascorbic acid) and vitamin E (tocopherol), food-approved antioxidants such as BHT and BHA (butylated hydroxytoluene, butylated hydroxyanisole), phenolic compounds and quinones, and highly hindered nitrogen free-radical scavangers such as 2,2,6,6-tetramethyl piperidine. Other drugs act by altering enzyme activity, and these may be very effective. Allopurinol, which inhibits the enzyme xanthine oxidase, substantially prevents the generation of superoxide, and has been found to be highly effective. Other xanthine oxidase inhibitors are also expected to be efficacious. Verapamil is known as a calcium-channel blocker, and is used as a vasodilator. It is highly effective in prevention of primary adhesions in the models described in the examples. Its mechanism of action is unknown, but it may prevent the stimulation of cells such as macrophages, which are believed to secrete active oxygen when stimulated. As defined herein, verapamil is an inhibitor of active oxygen.

Not all materials effective in prevention of adhesion formulation act against active oxygen. Other materials such as fibrinolytics can be used, including urokinase, tissue plasminogen activator, and ancrod. These materials alone may be effective, for example, as described by Dunn, et al., Am. J. Obstet. Gynecol. 164:1327–1330 (1991)), but enhanced when in combination with AOIs.

Formulations

The amount of AOI administered to the site will be adjusted to the particular site, and to the nature of the controlled release means being employed. A suitable starting amount is a single dose; this may then be adjusted upwards or downwards to optimize the amount. The results shown in the Examples below indicate that a broad optimum or plateau exists for SOD; many suitable AOIs, in other studies, also show broad effectiveness regions. The prolonged presence of low levels of the inhibitor at the injured site, provides not only protection in the immediate aftermath of surgery, but also minimizes damage and inflammation during at least the early stages of the healing process, and generally permits the use of lower effective doses.

The formulation of AOI and barrier materials should deliver AOI directly to the injured tissue over a period of days from about 0.5 day up to about 20 days under in vivo conditions. This is preferably controlled by the gel incorporating the AOI, but may also be provided by a mechanical barrier such as a membrane or fabric. The formulation may also contain additional means for regulating the release of the inhibitor, such as microspheres, microcapsules, microparticles or liposomes (referred to jointly herein as "microspheres"), especially when the AOI is a small molecule of less than about 20,000 daltons, where the AOI is released from the microspheres into the gel, from which it diffuses into the tissue, alone or in combination with release of AOI from the gel. Other means for controlled release include intact or comminuted gels, polymers with AOIs releasably bound thereto, and slowly dissolving particles of the AOIs or a complex thereof with an inert salt or organic molecule pratically. For example, verapamil as the free base is practically insoluble in water, while its hydrochloride is very soluble. Encapsulation of the liquid free base form in conventional timed-release microcapsules can be used to provide extended periods of delivery, by incorporating the microcapsules into the polymeric barrier.

The formulations may further contain excipients buffers, stabilizers, and other common additives, as known in the art of pharmaceutical formulation. The formulations may also contain ingredients needed for the formation of the barrier, such as polymerization-inducing or polymerization-enabling materials. These may include photoinitiators, chain transfer reagents, and co-monomers.

The formulation may be prepared in more than one container, for mixing just before use, and may be stabilized by lyophilization, freezing, dessication refrigeration, or other commonly used means. The formulation must be sterile; where ingredients of the formulation are unstable, filter sterilization and aseptic filling are prefered.

Methods of Treatment

Application of Formulations to Tissues

The formulation can be applied to the affected tissues by any suitable means. These include spraying, washing with a medication-containing fluid, spreading with an instrument or by hand, and direct implantation of a preformed inhibitor-containing barrier. When the barrier is a gel or other solid form, the gel may be implanted; preferably, however, a solution of the mixture of gel precursor and inhibitor to be delivered is delivered to the site of application, and gelled directly onto the tissue by an appropriate means. Preferred gelling means, because of their simplicity, are physical gelation due to a change in temperature or to a cessation of shear; and photopolymerization of a photoreactive gelling monomer. Chemical redox reactions, ionic crosslinking, and other methods of gel formation can also be utilized.

Instruments for performing delivery and gelling functions will be selected for the particular application, using principles and instruments known in the art. These will typically include catheters or laparoscopes for minimally invasive access to interior sites of the body; syringes for surface or surgically exposed sites such as in tendon or wound repair; and appropriate light sources when a polymerization reaction is required. Some suitable instruments are described in detail in U.S. Pat. Nos. 5,328,471, 5,213,580, and U.S. Ser. Nos. 08/054,385 (WO 94/24962), 08/036,128 (WO 94/21324), and 08/265,448, which are hereby incorporated by reference.

Medical Indications

Treatment with the compositions, medications and methods described herein is intended for any site in which adhesions form and have potential or actual deleterious effects. These include primary, and especially secondary, adhesions in the following: in the abdominal cavity, including intestine to intestine, and intestine to peritoneum; in the pelvic cavity, including adhesion of the uterus, ovaries or fallopian tubes to other structures including each other and the pelvic wall; in tendons and their support structures, including tendon to pulley or to synovium; in the repair of nerve sheaths; in repair of the spinal column or disks; in the pericardium; in treatment of joints for inflammation and to prevent pannus formation; and in any situation in which adhesions form which impair function or cause pain.

Moreover, the compositions may be used in other conditions in which an unwanted tissue proliferation occurs. These can include restenosis of arteries, repair of keloid or hypertrophic scars, hypertrophy which obstructs ducts, such as benign prostatic hypertrophy, and endometriosis.

The present invention will be further understood by reference to the following non-limiting examples. The following studies were designed to (1) demonstrate the potential for using locally delivered superoxide dismutase and (2)

to compare the efficacy of hydrogel-delivered SOD with hydrogel alone or SOD alone in the prevention of postsurgical adhesions.

EXAMPLE 1

Release of Model Compounds

The compatability of SOD protein with the components of the FocalGel system was tested in vitro. The compatibility of SOD with each component of the hydrogel system was tested step-wise, testing for any effect on SOD by gel electrophoresis, reversed phase HPLC, capillary electrophoresis and an enzymatic activity assay (cytochrome C). Since photopolymerization of the gel requires UV light, the effect of UV exposure (340–400 nm) on SOD stability was also evaluated.

Hydrogel Macromer (Pre-polymer) Preparation

In all pre-development studies, hydrogel was prepared in the same manner using the following method: Pluronic® F127 was added to a solution of potassium monobasic phosphate at pH 6.8. Photoinitiator (Irgacure® 651) was dissolved in tertiary butanol and added to the Pluronic®/buffer solution. Macromonomer and polyethylene glycol (PEG) 8000 were then added. Following sterile filtration, vials were filled and the water and t-butanol were removed by lyophilization. Prior to use in these studies, each vial of hydrogel was reconstituted with normal saline to arrive at a macromonomer/PEG 8000 concentration of 10% w/w, 3% w/w Pluronic®, and 1200 ppm Irgacure® 651.

A. Formulation Compatibility Studies.

SOD compatibility in the hydrogel formulation was evaluated using a step-wise study design. SOD stability in each formulation component was tested in the presence and absence of ultraviolet light exposure (365 nm). In these studies, protein stability was evaluated by gel electrophoresis (SDS-PAGE and native PAGE), HPLC, capillary electrophoresis and enzymatic activity by cytochrome C reduction.

Control samples were prepared by diluting one vial of SOD (15,000 U, 5 mg) with 1.5 mL PBS to give a final [SOD]=10 KU/mL. Additionally, 400 µL of this solution was diluted to 1 mL with PBS to give a final [SOD]=4 KU/mL. Irgacure®/F127-treated samples were prepared by adding 1.5 mL Irgacure®/F127 (1200 ppm and 3% w/w, respectively) to 1 vial of SOD (final [SOD]=10 KU/mL). For all UV-treated samples, 300 µL of sample solution was illuminated for either 20 or 60 seconds. Hydrogel-treated samples were prepared by adding 1.0 mL of hydrogel solution to a vial of SOD to give a final [SOD]=15 KU/mL. 200 µL of this solution was photopolymerized for either 20 or 60 seconds after 1.5 mL of PBS was added to the hydrogel. Samples were placed in an incubator at 37° C. for 24 hours prior to analysis.

Samples for electrophoresis were prepared by diluting 100 µL of sample with 300 µL of sample buffer (Bio-Rad technical manual LIT-188 REV C). Samples were not heated prior to analysis. 10 µL of sample was loaded onto the gel except for samples where SOD was released from hydrogel (20 µL used in these cases). Standards were run according to the vendor's protocol. Molecular weight bands in electrophoretic gels were integrated by image analysis.

There appears to be two low molecular weight subunit forms that are not identical, with the bulk of the protein existing as a tetrameric structure. To give a baseline for relative compatibility comparisons, SDS-PAGE of SOD was initially performed using a saline (no exposure) control. The data suggest that 92% of the protein exists as the high molecular weight form (67 kDa) with the remaining 8% existing as the low molecular weight monomer species (15.5 kDa). There was also a 12.7 kDa peak present, but the band intensity was very low and therefore not quantitated. Upon addition of the initiator and macromer formulation components, the relative band intensities remained nearly constant, and, with the addition of UV exposure, no visible changes were observed.

Native-PAGE analysis of SOD control solutions (SOD in PBS pH 7.4, [SOD]=1.33 and 3.33 mg/mL) shows single band SOD migration with band intensity directly related to protein content. Irgacure®/F127-treatment and hydrogel-extraction solutions display similar SOD band migrations and intensities as those displayed by the control.

SOD was incorporated into the initiator solution (3% F127 and 1200 ppm Irgacure®) by pipetting 2 mL of initiator solution into one vial containing SOD (final [SOD]=7.5 KU/mL). 300 µl aliquots of SOD/initiator were illuminated under the Black Ray lamp (power output=10 mW/cm2, lmax=365 nm). The results of analysis were analyzed as the total area of the SOD peaks, calculated SOD amount, expected SOD amount and percent recovery. Irgacure® levels in control solutions were also determined and compared to levels observed in the SOD/initiator samples.

SOD was also incorporated into hydrogel via bulk gel polymerization using 2 and 5 minute exposure times. Following polymerization, SOD was extracted from 200 µL bulk gels (8 mm×10 mm) over two days in PBS. Each of the extraction samples was analyzed for SOD amount and the cumulative amount was calculated as the % recovered of initial. The peak area of SOD in Irgacure®/F127 remained constant compared to the non-illuminated control after UV exposure (up to 5 min. exposure time). The data also show that the degradation products of Irgacure® photoinitiator in the control solutions were not altered in the SOD/Irgacure® treatment solutions. All degradation peaks observed in the samples were accounted for by Irgacure® degradation. Extraction of SOD from hydrogel resulted in 86.4 and 78.2% of the expected level recovered. The extraction was most likely not complete because SOD has been shown to be only partially released over 49 hours in vitro. Chromatograms for SOD extracted from Hydrogel show that peak distributions remained similar to those in control solutions.

Capillary testing was performed. In this set of experiments, a standard curve of SOD in water was prepared (1.48–11.84 KU/mL). SOD compatibility samples were prepared at 1.2, 1.6 and 11.9 KU/mL. Separation by CE shows that three sharp peaks are present (3.15, 3.20 and 3.27 minutes). The third peak has a shoulder which is a possible fourth peak. Each peak was integrated separately and the third peak was integrated to include the shoulder peak area. The standard curve of total peak area versus SOD concentration shows excellent linearity ($R^2$=1.000) over [SOD]= 1.48 to 11.84 KU/mL. The results show that the detected levels of SOD in Irgacure®/F127 (no illumination) were 130 and 82% of expected levels. When SOD/initiator samples were illuminated, the SOD levels remained high regardless of SOD concentration. Results from low [SOD] samples (1.2 KU/mL) showed more response variability than those prepared at higher concentrations (11.9 KU/mL). SOD extracted from bulk photopolymerized Hydrogel showed 89–108% of the expected SOD level recovered and the peak distribution remained similar to the SOD control.

Under standard assay conditions, cytochrome C ($10^{-5}$ M) reduction was measured at 25° C. with $5 \times 10^{-5}$ M xanthine oxidase (XOD) in 50 mM potassium phosphate buffer (pH 7.8) containing 0.1 mM EDTA. Inhibition of the reduction of cytochrome C by 50% was defined as 1 unit of SOD activity. Continuous spectrophotometric rate determination was performed over 5 minutes at 550 nm using a Hitachi UV/Vis spectrophotometer. Compatibility solutions were prepared and treated at [SOD]=5000 U/mL, then diluted with normal saline to a final [SOD]=10 U/mL. Relative specific activity was determined by comparing treatment solution activity to control solution activity ([control]=10 U/mL having 50% inhibition of cytochrome C reduction activity).

SOD in normal saline (10 U/mL, no illumination) was used as a control sample for relative compatibility comparison. The theoretical enzymatic activity as defined by the assay was 50% inhibition activity and the control solution showed the expected response (51.5% inhibition). Upon the addition of the initiator and/or macromer components, no dramatic change in the SOD activity was observed. Additionally, when SOD/hydrogel formulations were exposed to 1 min. of UV exposure, SOD activity levels (50.9% inhibition) were retained.

In vitro Release Characteristics

Subsequently, bulk photopolymerized hydrogel devices containing four levels of SOD (1, 3, 5, and 10 KU/mL) were prepared and evaluated for SOD in vitro release kinetics. SOD was dissolved in each of the individual components of the hydrogel prepolymer solution, in the presence or absence of ultraviolet light (10 mW/cm$^2$) and the SOD was then characterized by gel electrophoresis (SDS PAGE and native PAGE), reversed phase HPLC, capillary electrophoresis and enzymatic activity assay (as inhibition of cytochrome C reduction). No changes in protein characterization or enzymatic activity were observed using these techniques. The kinetics of release of SOD from bulk hydrogels were determined in vitro at hydrogel loads ranging from 1,000 to 10,000 U/mL.

10% macromer solutions were prepared using 1200 ppm Irgacure and 3% F127 in normal saline. To parallel the in vivo study design, four doses of SOD (1, 3, 5 and 10 KU/mL) were incorporated into the macromer solution and bulk photopolymerized in 200 µL aliquots (365 nm, 10 mW/cm2). SOD release in PBS was monitored over time using the micro-BCA method; activity of released SOD was also characterized using cytochrome C inhibition analysis.

The hydrogel cross-link density and the effective size of the molecular species are two major determinants of the drug release kinetics out of the hydrogel. In this case, three molecular weight species of SOD (67 kDa oligomer, 15.5 and 12.7 kDa monomers) are present. Based on data using dextran model compounds, it was expected that the low molecular weight species would completely elute from the gel within the first 12 hours and medium molecular weight species (67 kDa) would initially show a burst of release within the first 48 hours with prolonged release evident as the superficial diffusion zone is depleted.

The release of SOD from hydrogel in vitro in saline was biphasic. Hydrogels formed from 10% macromer solutions released 90% of the incorporated SOD within 48 hours ($t_{1/2}$=4 hours) with the remaining 10% being released by zero-order kinetics over the following 7 days ($t_{100}$=8 days). In contrast to the data obtained with dextran, the increase in the drug diffusion path length coupled with the hindered diffusivity of the larger molecular weight species results in extended durations of release to 8 days. Specific activity analysis of sample elution media demonstrates extended formulation stability.

EXAMPLE 2

Prevention of Primary Adhesions in Rat Model

Animal Models

In vivo efficacy experiments were performed in primary and secondary rat uterine horn adhesion models (RUHAM) to compare the relative efficacies of SOD when delivered by IP bolus versus controlled hydrogel delivery. Control groups included untreated (injured) and hydrogel (no SOD) animals. The final in vivo efficacy studies used dose-range study designs (1, 3, 5 and 10 KU/mL) in primary and secondary RUHAM models. The endpoint used for in vivo evaluation studies was 1 week post-treatment.

Experiments were performed using two rat uterine horn models which develop adhesions in response to an initial ischemic insult. The first model generates de novo adhesions (primary model) over a 7 day time period. The second model is a reformation (secondary) model whereby the fibrinous adhesions developed in the primary model are lysed and reformation of adhesions is observed 7 days after adhesiolysis. Forty sexually mature female Sprague-Dawley rats (225–250 grams) were used in the primary adhesion model. The animals were anesthetized following intramuscular injection of 4 mL/Kg of a mixture of ketamine (25 mg/mL), xylazine (1.3 mg/mL), and acepromazine (0.33 mg/mL). Aseptic technique was used throughout the surgical procedure. After preparing the abdomen, a 3 centimeter lower midline incision was made to expose the pelvic cavity. The uterine horns were positioned to expose the vascular arcade. Ischemia to the central portion of the uterine horns was induced by cauterizing the vascular arcade using bipolar electrocautery. Care was taken not to cauterize the most anterior and posterior vessels supplying blood to the horn to maintain minimal blood flow and ensure organ viability. Two additional injuries were made on the antimesenteric surface of the horn approximately 2.5 cm apart using electrocautery. Following surgical injury, animals were assigned to one of the four treatment groups in a random fashion. The musculoperitoneal layers and the overlying fascia were closed with a 4-0 vicryl absorbable suture and the skin incision closed using 7 mm stainless steel staples.

The animals were evaluated for adhesion formation at the end of one week. The "percent of adhesions" along the uterine horn is calculated as the measured length of the uterine horns engaged in adhesions divided by the entire length of the uterine horn multiplied by 100. The "percent efficacy" is 100 minus the "percent of adhesions."

In a second experiment, seven days after initiation of the primary adhesion model, animals (n=40) were opened and the uterine horns were exposed once again. Using microscopic surgical technique, adhesions between the uterine horns and other organs were carefully dissected and lysed. Bipolar electrocautery was used to maintain hemostasis. Upon completion of adhesiolysis, animals were assigned to different groups, treated according to protocol, and the peritoneal cavity was closed. Animals were evaluated at the end of a one week time period for adhesion reformation, and adhesion scores were calculated as described above.

In both the primary and secondary adhesion models, animals were assigned randomly to one of four groups according to the following experimental design:

Group 1: Control injury with no further treatment
Group 2: Hydrogel barrier alone
Group 3: SOD alone
Group 4: Hydrogel containing SOD For treatment Groups 2 and 4 (where Hydrogel was required), formulations were prepared as described above and 0.25 mLs of solution was applied onto the medial and lateral surface of the uterine horns for a total volume of 1 mL per animal. The preparation was subsequently photopolymerized by exposure to long wave ultraviolet light delivering an nominal irradiance of 20 mW/cm$^2$ for 20 seconds.

In Group 3, lyophilized SOD reconstituted with normal saline was dripped onto the surface of each uterine horn in 0.25 mL aliquots as described above. Four experiments were conducted to determine the effect of dose on primary and secondary adhesion formation. Doses ranging from 2,000 to 10,000 U/mL were compared when applied directly to peritoneal tissue and when added as a supplement to the Hydrogel formulation.

Results in Primary Adhesion Model.

The results are shown in FIG. 11. In all "untreated" control animals (Group 1), 93% or more of the uterine horn surface was adherent to adjacent mesometrium and/or organs resulting in efficacy scores of 7% or less. Hydrogel applied as a barrier to adhesion formation (Group 2) showed a broad range of efficacy values ranging from 11 to 46% efficacy. Application of SOD solution (Group 3) resulted in efficacy scores of 86–93%. Efficacy scores ranged from 79 to 85% when hydrogel containing SOD was applied (Group 4). No significant effect on efficacy was observed whether the bolus dose of SOD or SOD incorporated into Hydrogel, respectively, was 2,000 (10000 U/kg) or 10,000 U/mL (50,000 U/kg).

EXAMPLE 3

Prevention of Adhesion Reformation in Rat Model

Results in Secondary Adhesion Model.

Figure 2:
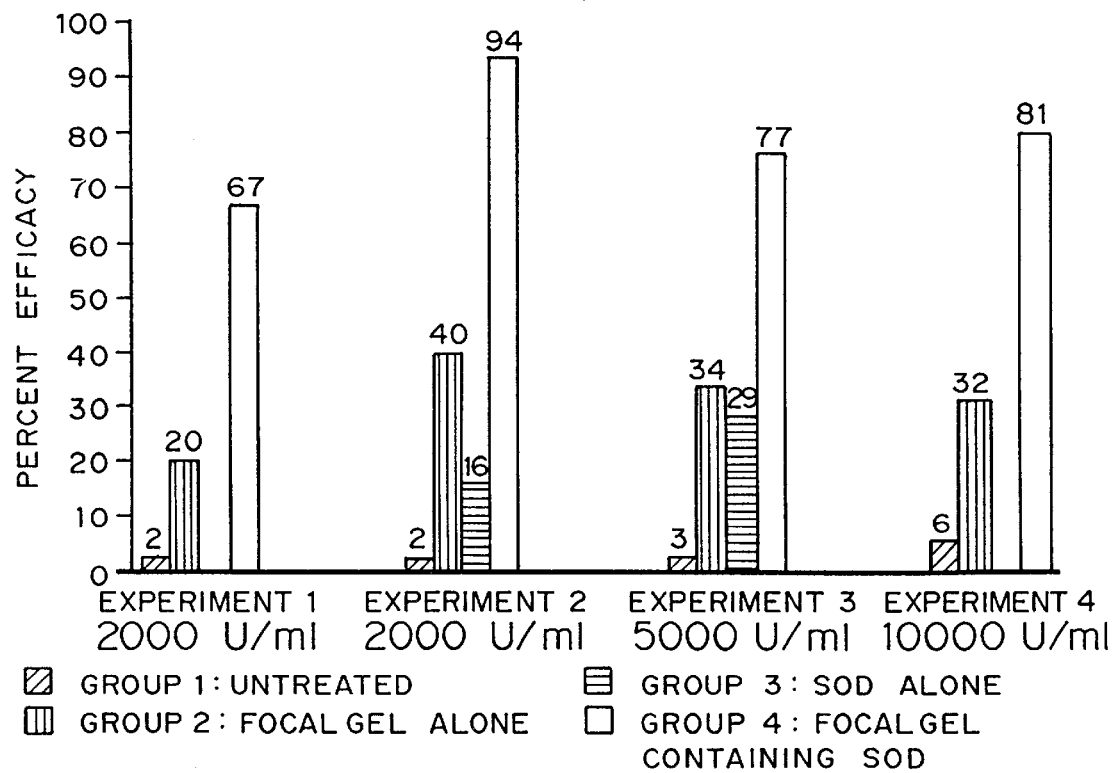
FIG. 2 is a bar graph of the percent efficacy in secondary adhesions rat uterine horn model of treatment with hydrogel (|| || ||), SOD alone (≡), and SOD locally delivered via the hydrogel (open bar), as compared with untreated animals (/ / /) at dosages of 2000 U SOD/ml, 5,000 U SOD/ml and 10,000 U SOD/ml.

The results are shown in FIG. 2. In all "untreated" control animals (Group 1), 94% or more of the uterine horn surface was adherent to the adjacent mesometrium or other organs resulting in efficacy scores of 6% or less. Hydrogel applied as a barrier to adhesion reformation (Group 2) resulted in efficacy scores of 20 to 40%. When SOD solution was applied (Group 3) scores ranged from 0 to 29%. Finally, application of SOD after incorporation into Hydrogel (Group 4) resulted in efficacy scores ranging from 67 to 94%. No significant effect on efficacy was observed when a bolus dose of SOD or a dose of SOD incorporated into Hydrogel, respectively, was 2,000, 5,000, or 10,000 U/mL.

Figure 3:
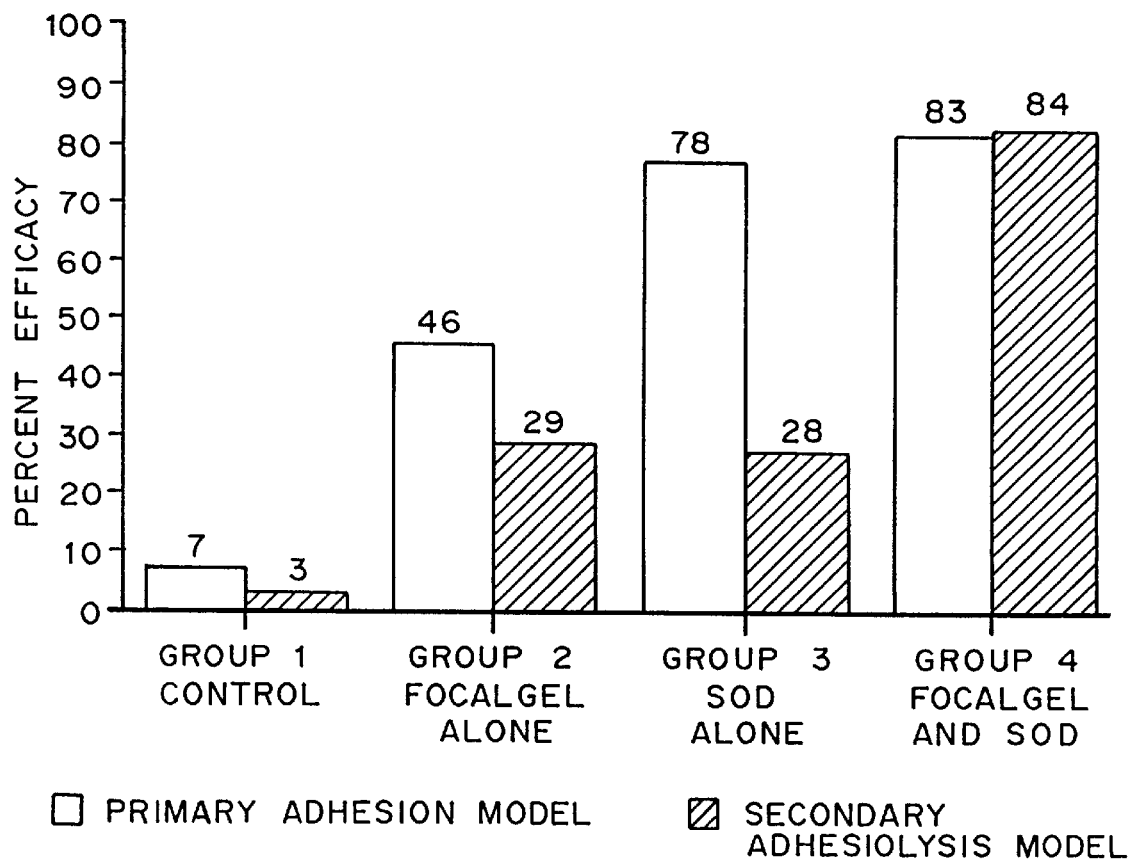
FIG. 3 is a bar graph of the percent efficacy of hydrogel (|| || ||), SOD alone and SOD locally delivered via the hydrogel compared with untreated animals (solid bar), for both primary (open bars) and secondary adhesion models.

Since no significant difference was found as a function of dose, the data from individual experiments were combined to summarize differences between treatment groups for both primary and secondary models, as shown in FIG. 3.

Diamond, et al., *Fert. and Ster.* 47:864 (1987); Peters, et al., *Br. J. Obstet. Gyn.* 99:59 (1992); Lucian, et al., *Obstet. & Gyn.* 74:220 (1989); Luciano, et al., *Fert. and Ster.* 48:1025 (1987); and Surrey, et al., *J. Repro. Med.* 27:658 (1982), have demonstrated that reduction of secondary adhesions is more difficult than primary adhesions in animal models. Based on the data presented here, it is likely that primary and secondary adhesions in rats are formed through different pathologic sequences. When histologic evaluations and the propensity for adhesion formation at the wound sites are compared, the differences between the two models become apparent. Lysis of fibrin followed by adhesion resorption occurs from day 7 through 28 in the primary model. In contrast, the secondary adhesion model results in persistent collagenous adhesions that do not resorb over an eight week period. These data indicate that there is a need for a pharmacologic intervention that lasts for a longer period of time to prevent secondary adhesions than a single bolus can provide. Adhesions formed in this secondary model are qualitatively similar to those experienced in the clinical situation. Although other formulations of hydrogel have produced efficacy in adhesion models, the particular formulation and application method used for this study provided marginal efficacy as a barrier. However, SOD loaded into the same formulation or the direct application of SOD solution to the uterine horns showed much higher efficacy in the primary model. This indicates that in this primary adhesion model, efficacy was produced by SOD due to early intervention in the pathologic sequence which is consistent with the production of oxygen-derived radicals during the initial stages of inflammation. Moreover, since the rate of elimination of SOD from blood is rapid, one may speculate that the efficacy shown by the bolus dose occurred in a short time frame. In the secondary model, there was a dramatic decline in efficacy when the barrier alone or a bolus of SOD was applied. However, a significant level of efficacy was achieved when the two modes of therapy were combined (i.e. the barrier loaded with SOD). This supports the hypothesis that more prolonged exposure to SOD is required when treating lysed, mature collagenous adhesions similar to those formed in the clinical population, rather than the short-lived fibrinous adhesions formed in the primary model.

Modifications and variations of the present invention will be obvious to those skilled in the art from the foregoing detailed description. Such modifications and variations are intended to come within the scope of the appended claims.

We claim:

1. A composition for the local alleviation of a medical condition caused by inflammation or unwanted tissue proliferation at a site, the composition comprising
   an effective amount of one or more active oxygen inhibitor compounds which destroy or prevent the formation of active oxygen species in a polymer solution or hydrogel, wherein the polymer solution or hydrogel is administered to the site in a fluent form and forms a conforming barrier by ionic crosslinking, chemical redox reaction, photopolymerization, or physical gelation at the site of administration, and
   wherein the barrier persists at the site for days to weeks.

2. The composition of claim 1, where the banier is degradable in vivo.

3. The composilion of claim 1, where the polymer solution is photopolymerizable.

4. The composition of claim 1, where the polymer solution or hydrogel comprises 0.5% to 80% by weight of the composition.

5. The composition of claim 4, where the polymer solution or hydrogel comprises 2% to 50% by weight of the composition.

6. The composition of claim 5, where the polymer solution or hydrogel comprises 4% to 30% by weight of the composition.

7. The composition of claim 1, where the active oxygen inhibitor compound is selected from the group consisting of superoxide dismutase, catalase, allopurinol, verapamil, and combinations thereof.

8. The composition of claim 7, where the inhibitor compound is superoxide dismutase.

9. The composition of claim 1 further comprising a biologically active compound other than an active oxygen inhibitor compound.

10. A method for the prevention of local inflammation or tissue proliferation, comprising administering a comprising an effective amount of an active oxygen inhibitor compound which destroys or prevents the formation of active oxygen species in combination with a polymer solution or hydrogel, wherein the polymer solution or hydrogel is administered to the site in a fluent form and forms a conforming barrier by ionic crosslinking, chemical redox reaction, photopolymerization, or physical gelation at the site of administration, and wherein the barrier persists at the site for days to weeks.

11. The method of claim 10, further comprising administering the composition in a pharmaceutically acceptable vehicle.

12. The method of claim 10, where the proliferation to be inhibited is the formation of an adhesion.

13. The method of claim 12, where the adhesion is a secondary adhesion.

14. The method of claim 10, where in the active oxygen inhibitor compound is selected from the group consisting of superoxide dismutase, catalase, allopurinol, verapamil, and combinations thereof.

15. The method of claim 14, where the inhibitor compound is superoxide dismutese.

16. The method of claim 10, wherein the active oxygen inhibitor compound is administered in a controlled release formulation.

17. The method of claim 10, where the barrier-forming material is a hydrogel-forming polymer.

18. The method of claim 10, further comprising administering at the site biologically active molecules that are not active oxygen inhibitors.

19. The method of claim 10, wherein the controlled release formulation is separate from the polymer solution or hydrogel forming the barrier.

20. The composition of claim 1, where the proliferation to be inhibited is the formation of an adhesion.

21. The composition of claim 20, where the adhesion is a secondary adhesion.

22. The composition of claim 1, further comprising in the polymer solution or hydrogel controlled drug delivery means for controlling the rate of delivery of the active oxygen inhibitor.

* * * * *